United States Patent [19]
Purcell, Jr. et al.

[11] Patent Number: 5,431,647
[45] Date of Patent: Jul. 11, 1995

[54] FIBEROPTIC CYLINDRICAL DIFFUSER

[75] Inventors: Earl E. Purcell, Jr., Westfield, Mass.; Ronald E. Hille, East Hartland, Conn.

[73] Assignee: Pioneer Optics Company, Windsor Locks, Conn.

[21] Appl. No.: 274,990

[22] Filed: Jul. 13, 1994

[51] Int. Cl.6 .................................. A61B 17/32
[52] U.S. Cl. ........................ 606/16; 606/15; 606/17
[58] Field of Search ............. 606/15, 16, 17, 10, 606/11, 12

[56] References Cited

U.S. PATENT DOCUMENTS

| 4,422,719 | 12/1873 | Orcutt . | |
|---|---|---|---|
| 4,466,697 | 8/1984 | Daniel . | |
| 4,648,892 | 3/1987 | Kittrell et al. . | |
| 4,660,925 | 4/1987 | McCaughan, Jr. . | |
| 4,693,556 | 9/1987 | McCaughan, Jr. . | |
| 4,899,188 | 2/1990 | Lecover . | |
| 4,989,933 | 2/1991 | Duguay . | |
| 4,995,691 | 2/1991 | Purcell, Jr. . | |
| 4,998,930 | 3/1991 | Lundahl . | |
| 5,042,980 | 8/1991 | Baker et al. . | |
| 5,054,867 | 10/1991 | Wagnieres et al. . | |
| 5,074,632 | 12/1991 | Potter | 385/31 |
| 5,125,925 | 6/1992 | Lundahl . | |
| 5,151,096 | 9/1992 | Khoury . | |
| 5,163,935 | 11/1992 | Black et al. | 606/17 |
| 5,169,395 | 12/1992 | Narcisco, Jr. . | |
| 5,190,538 | 3/1993 | Hussein et al. | 606/17 |
| 5,196,005 | 3/1993 | Doiron et al. . | |
| 5,207,669 | 5/1993 | Baker et al. . | |
| 5,209,748 | 5/1993 | Daikuzono . | |
| 5,217,456 | 6/1993 | Narciso, Jr. . | |
| 5,219,346 | 6/1993 | Wagniéres et al. . | |
| 5,242,438 | 9/1993 | Saadatmanesh et al. | 606/15 |
| 5,246,436 | 9/1993 | Rowe | 606/16 |
| 5,261,904 | 11/1993 | Baker et al. . | |
| 5,267,995 | 12/1993 | Doiron et al. . | |
| 5,269,777 | 12/1993 | Doiron et al. . | |

FOREIGN PATENT DOCUMENTS 1606128 11/1990 U.S.S.R. .

Primary Examiner—Stephen C. Pellegrino
Assistant Examiner—Sonya C. Harris

[57] ABSTRACT

A fiberoptic diffuser has an optical fiber having a light transmitting core, cladding about the core, and a buffer layer about the cladding. The core at the distal end portion of the fiber is exposed and a diffusing sleeve is disposed thereabout. A transparent cylindrical cap is disposed outwardly of the diffusing sleeve and overlies the exposed core, and a reflector is provided in the cap in axial alignment with the distal end of the core to reflect light rays exiting the core. The light rays exiting the core are reflected by the reflector and are refracted by the sleeve to exit through the cap over substantially the entire length of the exposed core.

21 Claims, 1 Drawing Sheet

FIBEROPTIC CYLINDRICAL DIFFUSER

BACKGROUND OF THE INVENTION

The present invention relates to fiberoptic devices and, more particularly, to a fiberoptic diffuser providing a generally cylindrical pattern of light emission.

In a number of medical procedures, it is necessary to deliver a uniform, cylindrical pattern of light as in the radiation of a cylindrical organ such as the esophagus. One such procedure is photodynamic therapy (PDT), which involves the use of light activated drugs for the treatment of cancers, tumors, or other diseases. The therapy requires that the tissue under treatment be infused with the photoactivatable medicinal composition, and then the tissue is irradiated with the triggering specific wavelength of light, typically a laser beam delivered by a fiberoptic wave guide.

It is an object of the present invention to provide a novel fiberoptic diffuser which will emit light in a generally uniform cylindrical pattern.

It is also an object to provide such a fiberoptic diffuser which may be fabricated relatively readily and which is relatively long lived and reliable in operation.

Another object is to provide such a fiberoptic diffuser in which the length of the cylindrical pattern of light emanating therefrom may be varied by facile variation of its components.

SUMMARY OF THE INVENTION

It has now been found that the foregoing and related objects may be readily attained in a fiberoptic diffuser comprising an optical fiber having a light transmitting core, cladding about the core, and a buffer layer about the cladding. The fiber has proximal and distal ends with the distal end portion of the fiber being free from the cladding and the buffer so as to expose the core. A diffusing sleeve is disposed about the exposed distal end portion of the core, and a transparent cylindrical cap is disposed outwardly of the diffusing sleeve and overlies the length of the exposed core. The cap has a mounting portion at one end secured to the buffer layer of the fiber.

A reflector is disposed in the cap in axial alignment with the distal end of the core to reflect light rays exiting the core. As a result, the light rays passing through the fiber and exiting the core are reflected by the reflector and are refracted by the sleeve to exit through the cap over substantially the entire length of the cap overlying the exposed distal end of the core.

In a preferred embodiment, the reflector is metallic with a specular surface; most desirably is formed of silver metal. Generally, the reflector has a concave reflecting surface, and desirably this is a conical recess.

Preferably, the sleeve is formed of a synthetic resin matrix with light scattering particles dispersed therewithin, and the sleeve is snugly seated upon the exposed core.

The cap is spaced radially outwardly from the sleeve to define a cavity therebetween, and the cavity is filled with air or with a transparent material having a low index of refraction.

Conveniently, the mounting portion of the cap is generally tubular, and preferably it is internally threaded and threadably engaged upon the buffer layer of fiber.

DETAILED DESCRIPTION OF THE PREFERRED EMBODIMENT

Figure 1:
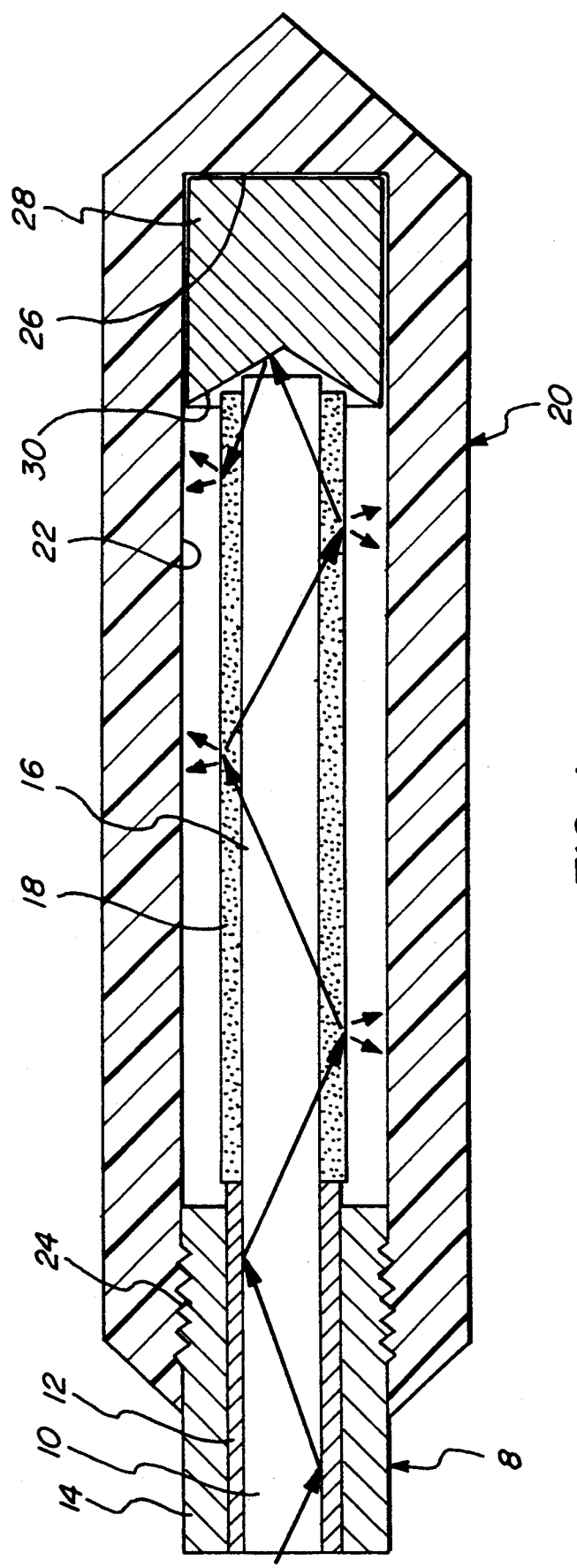
FIG. 1 is a fragmentary sectional view of a fiberoptic diffuser embodying the present invention with arrows indicting the paths of light rays.

As seen in FIG. 1, a fiberoptic diffuser embodying the present invention employs a fiberoptic light guide generally designated by the numeral 8 and having a core 10, cladding 12 extending about the core 10, and an outer buffer layer 14. The distal end portion 16 of the core 10 is free from cladding 12 and buffer layer 14. The distal tip of the fiber core is cleaved or polished to a flat perpendicular to the axis of the core 10.

Mounted on the distal end portion 16 of the fiber 8 is a diffuser sleeve 18, and extending thereabout is a generally cylindrical cap generally designated by the numeral 20 providing an axially extending cavity 22 of circular cross section. As seen, the outer end of the cavity 22 is internally threaded as indicated by the numeral 24 to engage the buffer layer 14, and the inner end 26 of the cavity 22 is spaced from the distal end of the core 10. Seated at the inner end of the cavity 22 is a silver mirror generally designated by the numeral 28 which has a conical recess 30 in its face adjacent the core 10.

Light rays travel down the core of the optical fiber 8 to the distal end portion of the fiber 8 where the fiber buffer 14 and cladding 12 have been replaced with the diffusing sleeve 18. At this portion 16 of the fiber 8, the fiber core 10 and diffusing sleeve 18 combine to act as the fiber core with the air space in the cavity 22 between the sleeve 18 and cap 20 acting as cladding. Light rays in this section of the fiber reflect off the diffusing sleeve/air interface. Some of the light rays strike scattering particles in the diffusing sleeve 18 and are reflected down the fiber. This rate of scattering is controlled by the density of the scattering particles in the matrix and the thickness of the diffusing sleeve 18. Longer diffusers require lower scattering particle density; shorter diffusers require higher scattering particle density.

As light is gradually scattered outwardly of the fiber 8, the light energy remaining in the fiber 8 decreases. This decreased core energy means that less light is available to be scattered. Therefore, the scattered light output tends to be higher where the light enters the area of the diffusion sleeve 18 and diminishes toward the distal end of the core 10. However, when the light energy remaining in the core 10 is reflected by the mirror 28, the scattered light intensity profile is reversed. Of the light rays returning into the fiber 8, more light is available to be scattered at the distal end. This means that more energy is scattered at the distal end, and less as the light travels back along the fiber core 10. The result of adding these two opposed, diminishing scattering outputs is scattering which tends toward uniformity. By making the reflecting mirror 28 at the distal end of the fiber core 10 with the concave surface 30, low order light rays are reflected by the concave surface 30 of the mirror 28 into higher order light rays.

The angle of the concave surface 30 can be adjusted to achieve the desired scattering output pattern. Some of the light reflected from the mirror 28 is not scattered and is wasted by traveling back up the optical fiber. (It has been found that, with proper design, a minimum of energy is wasted). The scattering material density, diffusing sleeve thickness, mirror concavity angle, and diffuser length are designed to achieve the desired scattered light output profile.

The diffusing sleeve may be fabricated from various materials providing the desired diffusion characteristics. Preferably, the material employed for the matrix is an optically clear transparent resin, and light scattering particles are uniformly dispersed within this matrix. The preferred resins are polyesters although other resins such as epoxies, acrylics, polyvinyl chloride and polyolefins may also be employed.

The dispersed material is conveniently titanium dioxide pigment particles although other materials such as alumina, zinc oxide and the like may also be employed.

By providing the sleeve 18 as a heat shrinkable tubing, it may be snugly secured to the core 10. The inside diameter of the shrink tube 18 must have a tight tolerance with the fiberoptic core 10 to provide total contact with the core 10. This can be monitored during the assembly process by illuminating the fiber 8 with a helium/neon laser. The desired output can be achieved by adjusting the concentration of scattering material in the heatshrink tubing and the thickness of the tubing. Although typically a uniform output is desirable, a custom output pattern may be achieved by using different heatshrink tubing sections along the length of the fiber core 10. In the preferred embodiment, the density range of the titanium dioxide in the shrink material would be clear to a 30:1 let-down ratio. The longer length diffusers require lower scattering material concentration or a thinner wall, section and the shorter length diffusers require a higher concentration of diffuser material or a thicker wall section.

The cap 20 is fabricated of an optically clear material such as polycarbonate resin and is conveniently machined from rod stock. In addition to the threaded engagement provided by a thread formed in the cavity of the cap 20, adhesives may also be employed. Moreover, adhesives may be used as the sole means of attachment as can be crimping.

The housing cavity 22 is of a larger diameter than the outer diameter of the diffusing sleeve 18, so as to allow for an air gap over the entire surface of the diffusing sleeve 18. This air gap acts as a cladding for the composite "core" consisting of the diffusing sleeve 18 and fiber core 10. The cap 20 is threaded onto the buffer layer 14 to an extent that allows the periphery of the tip of the fiber core 10 to contact the surface of the beveled mirror 28.

The mirror 8 must be manufactured from a highly reflective material. Fine silver (99.9% pure) is the preferred material, but other materials such as gold, platinum, etc., may be used. In a preferred embodiment, the concave mirror surface 30 is a 20° bevel with a surface finish of 8 microinches or better. Other mirror configurations from a polished flat surface up to a 45° concave bevel could be used. The mirror's outer diameter is sized to provide a line on line to slightly loose fit within the cavity 22 of the cylindrical cap 20. The length of the mirror 28 can vary dependent on cap length and need for providing a satisfactory heat sink. The length in the preferred embodiment ranges from 0.030"–0.050".

As a specific example of a fiberoptic diffuser embodying the present invention, an optical fiber supplied by Minnesota Manufacturing and Mining Corporation under the designation FT-400-UMT has its distal end portion stripped by using a fiber buffer strip tool to remove the buffer layer, and acetone to remove the cladding. A portion of the core adjacent the distal end is preferably free from the diffusing sleeve because it is desirable to remove the cladding and buffer layer for some distance behind the tip so as to remove these heat sensitive materials from the point of high output light intensity. The air surrounding the bare core will function as "cladding" to preclude any substantial light egress through the unclad portion adjacent the tip.

The end of the core is conveniently cleaved flat. This flat configuration may also be achieved by use of a fine polishing paper.

The cap is conveniently machined from a 0.065 inch diameter rod of polycarbonate resin. The internal thread is conveniently 000-120 standard thread, and a wicking adhesive sold by Loctite Corporation under the name PRIZM 408 is used to firmly lock the cap to the buffer layer of the fiber.

The heat shrinkable diffusing sleeve is a polyester film containing titanium dioxide and has a wall thickness of 0.0005 inch.

Tests utilizing the fiberoptic diffuser of the present invention establish that the light rays are emitted over the length of the arc, thus providing the desired length of relatively uniform light emission for irradiation of cylindrical organs. In a 2.5 cm diffuser length, a uniform intensity tolerance of $+/-30\%$ was easily achieved. The configuration and construction of the diffuser allows higher energy inputs by minimizing heat concentration and the assembly is relatively rugged.

Thus, it can be seen that the fiberoptic diffuser of the present invention is one which offers significant advantages for photodynamic therapy and minimizes the risk of over-radiation of a small area of the organ being treated. The diffuser may be fabricated readily and relatively economically, and considerable variation in the pattern of radiation can be effected by changes in the configuration of the diffusing sleeve and concavity of the mirror and cap.

Having thus described the invention, what is claimed is:

1. A fiberoptic diffuser comprising:
   (a) an optical fiber having a light transmitting core, cladding about said core, and a buffer layer about said cladding, said fiber having proximal and distal ends with a portion of said fiber adjacent said distal end being free from said cladding and said buffer to expose said core;
   (b) a diffusing sleeve disposed about said exposed distal end portion of said core;
   (c) a transparent cylindrical cap spaced outwardly of said diffusing sleeve and overlying said exposed core, said cap having a mounting portion at one end secured to said buffer layer of said fiber; and
   (d) a reflector in said cap in axial alignment with the distal end of said core and configured to reflect light rays exiting said core back into said core and sleeve, whereby light rays passing through said fiber and exiting said distal end of said core are reflected by said reflector and whereby light rays passing into said sleeve are refracted by said sleeve to exit through said cap over substantially the entire length of said cap overlying said exposed distal end of said core.

2. A fiberoptic diffuser in accordance with claim 1 wherein said reflector is metallic with a specular surface.

3. A fiberoptic diffuser in accordance with claim 2 wherein said reflector is formed of silver metal.

4. A fiberoptic diffuser in accordance with claim 1 wherein said reflector has a concave reflecting surface.

5. A fiberoptic diffuser in accordance with claim 4 wherein said concave reflecting surface is a conical recess.

6. A fiberoptic diffuser in accordance with claim 1 wherein said sleeve is formed of a synthetic resin matrix with light scattering particles dispersed therewithin.

7. A fiberoptic diffuser in accordance with claim 1 wherein said sleeve is snugly seated upon said exposed core.

8. A fiberoptic diffuser in accordance with claim 1 wherein said cap is spaced radially outwardly from said sleeve to define a cavity therebetween.

9. A fiberoptic diffuser in accordance with claim 8 wherein said cavity is filled with air.

10. A fiberoptic diffuser in accordance with claim 8 wherein said cavity is filled with a transparent material having a low index of refraction.

11. A fiberoptic diffuser in accordance with claim 1 wherein said mounting portion of said cap is generally tubular.

12. A fiberoptic diffuser in accordance with claim 11 wherein said mounting portion of said cap is internally threaded and threadably engaged upon said fiber.

13. A fiberoptic diffuser comprising:
(a) an optical fiber having a light transmitting core, cladding about said core, and a buffer layer about said cladding, said fiber having proximal and distal ends with a portion of said fiber adjacent said distal end being free from said cladding and said buffer to expose said core;
(b) a diffusing sleeve disposed about said exposed distal end portion of said core;
(c) a transparent cylindrical cap spaced outwardly of said diffusing sleeve to provide a cavity therebetween and overlying said exposed core, said cap having a mounting portion at one end secured to said buffer layer of said fiber; and
(d) a concave reflector with a specular metal surface in said cap in axial alignment with the distal end of said core to reflect light rays exiting said core back into said core and sleeve, whereby light rays passing through said fiber and exiting said core are reflected by said reflector and whereby light rays passing into said sleeve are refracted by said sleeve to exit through said cap over substantially the entire length of said cap overlying said exposed distal end of said core.

14. A fiberoptic diffuser in accordance with claim 13 wherein said reflector is formed of silver metal.

15. A fiberoptic diffuser in accordance with claim 13 wherein said concave reflecting surface is a conical recess.

16. A fiberoptic diffuser in accordance with claim 13 wherein said sleeve is formed of a synthetic resin matrix with light scattering particles dispersed therewithin.

17. A fiberoptic diffuser in accordance with claim 13 wherein said sleeve is snugly seated upon said exposed core.

18. A fiberoptic diffuser in accordance with claim 13 wherein said cavity is filled with air.

19. A fiberoptic diffuser in accordance with claim 13 wherein said cavity is filled with a transparent material having a low index of refraction.

20. A fiberoptic diffuser in accordance with claim 13 wherein said mounting portion of said cap is generally tubular.

21. A fiberoptic diffuser in accordance with claim 20 wherein said mounting portion of said cap is internally threaded and threadably engaged upon said fiber.

* * * * *